United States Patent [19]
Lee et al.

[11] Patent Number: 5,946,096
[45] Date of Patent: Aug. 31, 1999

[54] HETERODYNE INTERFEROMETRY METHOD FOR MEASURING PHYSICAL PARAMETERS OF MEDIUM

[75] Inventors: King-Hung Lee; Chuan-Chuan Chen; Horn-Haw Chen; Der-Chin Su, all of Hsinchu; Ming-Horng Chiu, Feng-Yuan, all of Taiwan

[73] Assignee: Industrial Technology Research Institute, Hsinchu, Taiwan

[21] Appl. No.: 08/888,658

[22] Filed: Jul. 7, 1997

[30] Foreign Application Priority Data

May 9, 1997 [TW] Taiwan ............................... 862070901

[51] Int. Cl.[6] ...................................................... G01B 9/02
[52] U.S. Cl. ........................... 356/349; 356/351; 356/361
[58] Field of Search ..................................... 356/345, 351, 356/349, 361

[56] References Cited

PUBLICATIONS

Rohlin, "An Interferometer for Precision Angle Measurements", *Appl. Opt.* 2 (7), pp. 762–763 (Jul. 1963).
Malacara et al. "Interferometric Measurement of Angles", *Appl. Opt.* 9 (7), pp. 1630–1633 (Jul. 1970).
Ulrich et al., "Measurement of thin film parameters with a prism coupler", *Appl. Opt.* 12(12), pp. 2901–2908 (Dec. 1973).
Chapman, "Interferometric Angular Measurement", *Appl. Opt.* 13 (7), pp. 1646–1651 (Jul. 1974).
Yoder et al., "Active annular–beam laser autocollimator system", *Appl. Opt.* 14 (8), pp. 1890–1895 (Aug. 1975).
Born et al., *Principles of Optics,* 6th ed., Pergamon Press, Oxford, U.K., pp. 48–50 (1980).
Kitajima et al., "Use of a total absorption ATR method to measure complex refractive indices of metal–foils", *J. Opt. Soc. Am,* 70(12), pp. 1507–1513 (Dec. 1980).
Kirsch, "Determining the refractive index and thickness of thin films from prism coupler measurements", *Appl. OPt.* 20 20(12), pp. 2085–2089 (Jun. 1981).
Ennos et al. "High accuracy profile measurements of quasi–conical mirror surface by laser autocollimation", *Precis. Eng.* 4(1), pp. 5–8 (Jan. 1982).
Azzam, "Simple and direct determination of complex refractive index and thickness of unsupported or embedded thin films by combined reflection and transmission ellipsometry at 45° angle of incidence", *J. Opt. Soc. Am.*, 73, pp. 1080–1082 (1983).
Azzam, "Maximum minimum reflectance of parallel–polarized light at interfaces between transparent and absorbing media", *J. Opt. Soc. Am.* 73(7), pp. 959–962 (Jul. 1983).
Schuda, "High–precision, wide–range, dual–axis, angle monitoring system", *Rerv. Sci. Instrum.* 54 (12), pp. 1648–1652 (Dec. 1983).
Luther et al., "Single axis photoelectronic autocollimator", *Rev. Sci. Instrum.* 55 (5), pp. 747–750 (May 1984).
Jarvis et al., "Critical–angle measurement of refractive index of absorbing materials: an experimental study", *J. Phys. E. Sci. Instrum.*, 19, pp. 296–298 (1986).
Shi et al., "New optical method for measuring small–angle rotations", *Appl Opt.* 27 (20), pp. 4342–4344 (Oct. 1988).
Beck et al., "Evaluation of optical properties of decorative coating by spectroscopic ellipsometry", *Thin Solid Films,* 220, pp. 234–240 (1992).

(List continued on next page.)

*Primary Examiner*—Robert H. Kim
*Attorney, Agent, or Firm*—Merchant & Gould, P.C.

[57] ABSTRACT

A new method for measuring refractive index, small angle, pressure or temperature is disclosed. The method of the present invention utilizes a heterodyne interferometry technique to measure the phase difference between s-(vertical) and p-(horizontal) polarizations, and then substitutes the difference into Fresnel's equations so as to obtain the physical values of the medium to be tested, such as refractive index, small angle, pressure or temperature.

7 Claims, 2 Drawing Sheets

OTHER PUBLICATIONS

Akimoto et al., "Brewster and pseudo–Brewster angle technique for determination of optical constants", *Jpn. J. Appl. Phys.*, 31, pp. 120–122 (Jan. 1992).

Huang et al., "Angle measurement based on the internal-reflection effect: a new method", *Appl Opt.* 31 (28), pp. 6047–6055 (Oct. 1992).

Nee et al., "Accurate null polarimetry for measuring the refractive index of transparernt materials", *J. Opt. Soc. Am. A.* 10, pp. 2076–2083 (1993).

Shi et al., "Improving the linearity of the Michelson interferometric angular measurement by a parameter compensation method", *Appl. Opt.* 32 (1), pp. 44–51 (Jan. 1993).

Wang, "Determination of optical constants of absorbing thin films from relectance and transmittance measurements with oblique incidence", *J. Opt. Soc. Am.* A, 11 (8), pp. 2331–2337 (Aug 1994).

Levesque et al., "Precise thickness and refractive index determination of polymide films using attenuated total reflection", *Appl. Opt.* 33(34), pp. 8036–8040 (Dec. 1994).

Rigneault et al., "Nonlinear totally reflecting prism coupler: thermomechanic effects and intensity–dependent refractive index of thin films", *Appl. Opt.* 34 (21), pp. 4358–4369 (Jul. 1995).

Huang et al., "Angle measurement based on the internal–reflection effect and the use of right–angle prisms", *Appl. Opt.* 34 (22), pp. 4976–4981 (Aug. 1995).

Chiu et al., "Refractive–index measurement based on the effects of total internal reflection and the uses of heterodyne interferometry", *Appl. Opt.* 36 (13), pp. 1–4 (May 1997).

Chiu et al., "Angle measurement using total–internal–reflection heterodyne interferometry", *Opt. Eng.* 36 (6), pp. 1–4 (Jun. 1997).

HETERODYNE INTERFEROMETRY METHOD FOR MEASURING PHYSICAL PARAMETERS OF MEDIUM

FIELD OF THE INVENTION

The invention relates to an common path heterodyne interferometry, and more particularly, to a total internal reflection heterodyne interferometry (TIRHI) combining total internal reflection characteristics for measuring physical values of a medium to be tested, wherein the two important physical parameters (refractive index and incident angle) can be viewed as physical variations. The method of the present invention is mainly used to measure the physical values such as refractive index, small angle, pressure and temperature of an optic-electro material.

BACKGROUND OF THE INVENTION

There are a plurality of interferometries and interferometers which are used to make optical and non-contact measurements, but most of the interferometries and interferometers are not in common path structure. Therefore, there are following problems:

(1) In a non-common path structure, the optical path difference between the mutually interfered reference beam and test beam should be within the coherent length. Besides, the contrast of the interference signal will decrease when the optical path difference is increased.

(2) In a non-common path structure, the environment of the two light beams should be strictly controlled. For example, the air disturbance and the outer vibration should be avoided. Besides, the pressure, temperature and humidity of the control room are also necessary to be controlled stably and effectively.

(3) The analysis of the interference fringes is more complex, troublesome and less precise.

The heterodyne interferometry carries the physical values to be tested in the phase of the interference signal rather than the amplitude of the interference signal. Therefore, the change of the light intensity during the interfered process will not effect the measurement result. The physical value to be tested can be retrieved from the phase of the interference signal in real time, and this is the unique characteristic of heterodyne interferometry. However, if the heterodyne interferometry is not used in a common path structure, it still has disadvantages such as the above-mentioned (1) and (2) and the measurement precision will be decreased.

Refractive index is a very important characteristic parameter of optical materials. There are a plurality of measuring methods proposed such as critical angle method, prism couple method, Brewster angle method and total reflection method. All of these methods utilize the change of the light intensity of the reflection beam or transmission beam to derive the refractive index. However, such methods for measuring the refractive index of the materials to be tested by the light intensity have two main disadvantages:

(1) The measurement precision is easily decreased by outer light source or scattering light source when the refractive index is measured by light intensity, thus it is better to measure the medium to be tested in a darkroom so as to isolate the unnecessary light sources. Therefore, it is inconvenient to operate the interferometer in a bright room. Besides, the light source should have a very stable single wavelength.

(2) The measurement of the unnecessary reflection light and scattering light among the boundary will be varied by the different incident angles, thus the error compensation of the light intensity will be more troublesome. The measurement precision will be decreased by the light source stability, medium absorption, scattering light and the reflection light from other boundary to be tested. Besides, the refractive index measurement should firstly obtain the thickness of the medium to be tested, and the interference signal is easily effected by the environment disturbance.

In the angle measurement, it is conventionally to measure the rotation angle of a medium by mechanic scaling. However, an optical measurement, such as interferometer or autocollimator, is applied when some precision and non-contact requirements are necessary. Though the method has advantage such as high resolution, such a method requires a large space. It is hard to apply such a measurement system in a limit space.

SUMMARY OF THE INVENTION

In view of the drawbacks of the prior art, it is an object of present invention to provide a measuring method for measuring physical values which are reacted to the refractive index or angle. The relationship between the variation of refractive index or angle and the variation of the phase difference after the total internal reflection is firstly obtained so as to derive the physical value to be tested. Therefore, it is necessary to firstly obtain the relationship between the variation of refractive index or angle and the variation of the phase difference after the total internal reflection. The present invention measures the phase difference which is independent to the light intensity variation and increase the measurement precision.

The present invention mainly utilizes a light source with a frequency difference between the s-polarization (vertical) and p-polarization (horizontal) which is incident on the boundary of a prism (the refractive index is known) and the medium to be tested. In this boundary, a phase difference between the s-polarization and p-polarization is generated due to the total internal reflection. Such a phase difference is associated with the refractive index to be tested and the incident angle. The reflection beam after total internal reflecting passes through an analyzer with respect to the transmission axis at 45°, the vectors at 45° of the s-polarization and p-polarization are interfered mutually and are detected by photodetectors. The interference signal is a sinusoidal signal with a frequency difference between two polarizations, e.g. the beat frequency in the interferometry. Such a signal and the reference signal is compared by a phase meter and the phase difference due to the total internal reflection is obtained. The obtained phase difference is finally calculated via Fresnel's equation operation by a personal computer or an electronic hardware. The refractive index of the medium to be tested is thus obtained in real time. If the refractive index of the medium to be tested is varied, the variation of the refractive index can be derived from the variation of the phase difference. Besides, if the two refractive indexes on the total internal reflection boundary are known, the variation of angle can also be derived from the variation of the phase difference.

It is another object of the present invention to provide a method for measuring other physical values such as pressure, temperature and concentrations of liquid and gas. As long as the physical values to be tested will cause the variations of refractive index or angle, the present invention can be applied.

It is still further an object of the present invention to overcome the disadvantages of the interferometry or interferometer with non-common path structure and to provide an easy analysis, easy operation, low cost and stable measuring method so as to solve the high precision measurement problems.

BRIEF DESCRIPTION OF THE DRAWINGS

For a more complete understanding of the present invention and the advantages thereof, reference is now made to the following descriptions taken in conjunction with the accompanying drawings which illustrate one or more embodiments of the present invention.

DETAILED DESCRIPTION OF THE INVENTION

Figure 1:
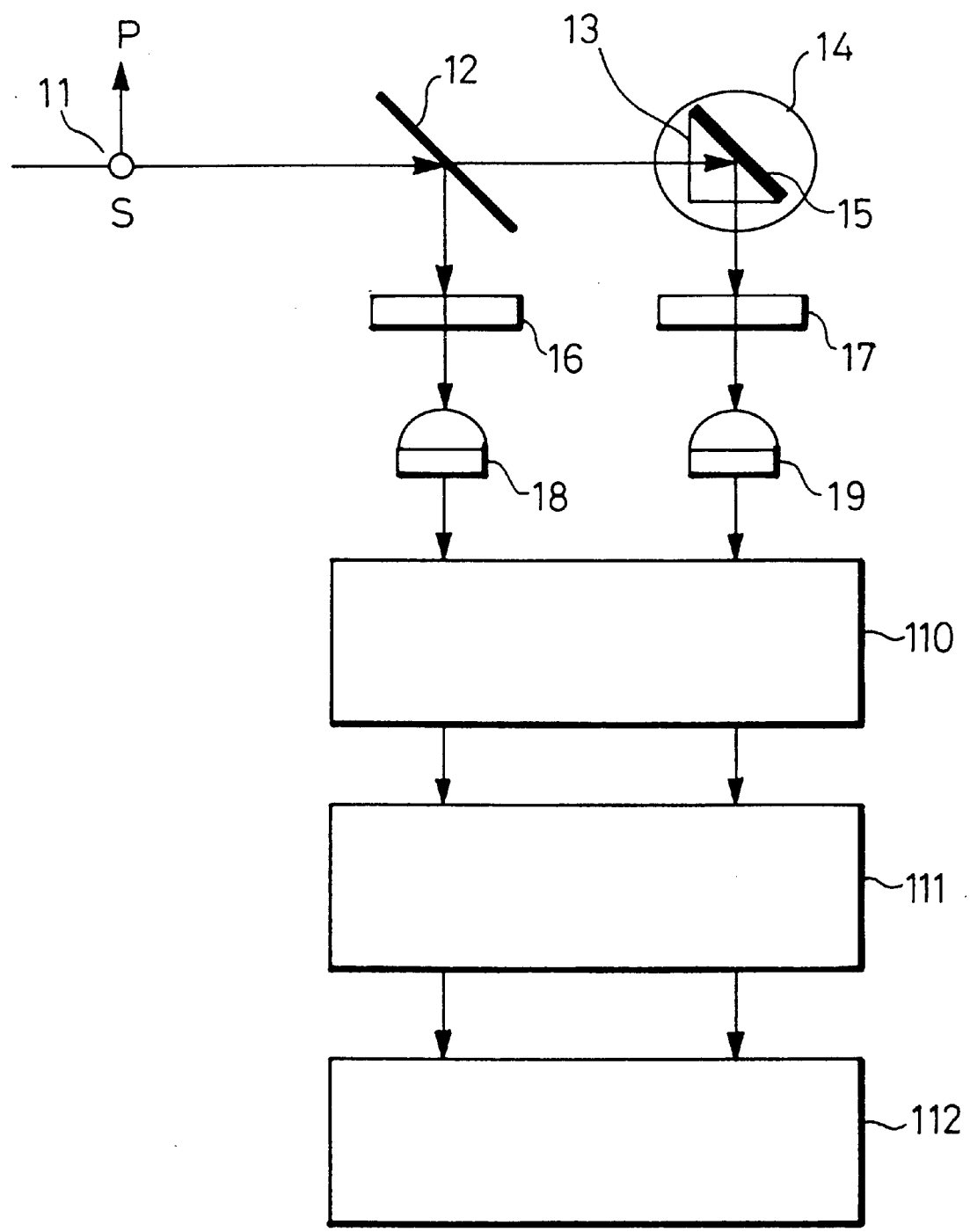
FIG. 1 illustrates a schematic diagram for measuring refractive index or incident angle of the medium to be tested by TIRHI of the present invention.
Figure 2:
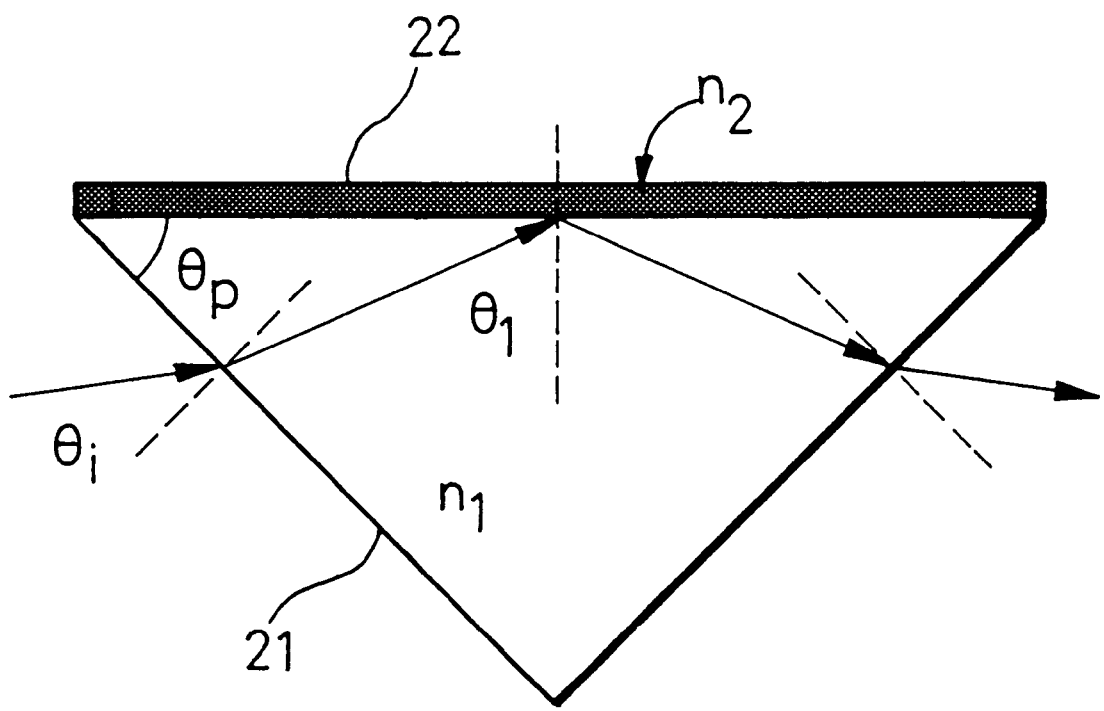
FIG. 2 illustrates the light path of the total internal reflection at the boundary.

Referring to FIG. 1, the main structure of the present invention are constituted by a light source 11 (heterodyne light source) with a frequency difference between the s-polarization and p-polarization, beam splitter 12, isosceles prism 13, rotary stage 14, two analyzers 16 and 17 with transmission axes at 45°, two photodetectors 18 and 19, phase meter 110, personal computer or automatic operation processing hardware 111 and display 112. The medium to be tested 15 is tightly positioned at the bottom side of the isosceles prism 13. The incident beam is divided into reflection beam and transmission beam. The reflection beam passes through the analyzer 16 and is detected by the photodetector 18 so as to obtain the following mathematical type signal:

$$I_r = \frac{1}{2}(1 + \cos(2\pi f t + \psi)) \quad (1)$$

wherein is the initial phase difference between the s-polarization and p-polarization, f is the frequency difference between the s-polarization and p-polarization and $I_r$ is the reference signal. On the other hand, the transmission beam passes through prism 13 and is totally internally reflected at the boundary of the medium to be tested 15. The totally internally reflected signal passes through the analyzer 17 and is detected by the photodetector 19 so as to obtain the following mathematical type signal:

$$I_t = \frac{1}{2}(1 + \cos(2\pi f t + \psi - \phi)) \quad (2)$$

wherein $I_t$ is the signal to be tested in the total internal reflection heterodyne interferometry, $\phi$ is the phase difference between the s-polarization and p-polarization after the total internal reflection. The signals $I_r$ and $I_t$ are transmitted into the phase meter 110 and are compared so as to obtain the $\phi$. The relation between $\phi$ and the refractive index of the medium to be tested can be described as following:

Referring to FIG. 2, according to Snell's law and the light ray refracted into the prism and propagated toward the base surface of the prism; an isosceles prism 21 with known refractive index $n_1$ and base angle $\theta_p$; the medium to be tested 22 with refractive index $n_2$ is tightly positioned on the bottom side of the isosceles prism 21; the s- and p-polarization are incident on one side of the isosceles prism at $\theta_i$; the incident angle on the boundary is $\theta_1$; thus we have $$\theta_1 = \theta_p + \sin^{-1}\left(\frac{\sin\theta_i}{n_1}\right) \quad (3)$$

Because the method of the present invention is operated under the total internal reflection condition, the refractive index $n_1$ should be greater than the refractive index $n_2$. According to Fresnel's equation, the coefficients of reflection of the s-polarization and p-polarization can be respectively expressed as $$r_s = \frac{\cos\theta_1 - i\sqrt{\sin^2\theta_1 - n^2}}{\cos\theta_1 + i\sqrt{\sin^2\theta_1 - n^2}} = e^{i\delta_s} \quad (4)$$

and $$r_p = \frac{n^2\cos\theta_1 - i\sqrt{\sin^2\theta_1 - n^2}}{n^2\cos\theta_1 + i\sqrt{\sin^2\theta_1 - n^2}} = e^{i\delta_p} \quad (5)$$

wherein $n=n_2/n_1$ (the refractive index ratio), $\delta_s$ and $\delta_p$ are the phase delay of the s-polarization and p-polarization generated by the total internal reflection. Therefore, the phase difference between the s-polarization and p-polarization is $$\phi = 2\tan^{-1}\left(\frac{\sqrt{\sin^2\theta_1 - n^2}}{\tan\theta_1 \sin\theta_1}\right) \quad (6)$$

Substituting Eq. (1) into Eq. (4), we have $$\phi(n, \theta_i) = 2\tan^{-1}\left(\frac{\sqrt{\sin^2[\theta_p + \sin^{-1}(\sin\theta_i/n_1)] - n^2}}{\tan(\theta_p + \sin^{-1}(\sin\theta_i/n_1))\sin(\theta_p + \sin^{-1}(\sin\theta_i/n_1))}\right) \quad (7)$$

which can be rewritten as $$n = \sin(\theta_p + \sin^{-1}(\sin\theta_i/n_1))\left[1 - \tan^2\left(\frac{\phi}{2}\right)\tan^2(\theta_p + \sin^{-1}(\sin\theta_i/n_1))\right]^{\frac{1}{2}} \quad (8)$$

Therefore, the refractive index ratio n can be obtained by the personal computer or automatic operation processing hardware 111 with the measurement of $\phi$ and incident angle $\theta_i$ measured by the phase meter 110. The refractive index $n_2$ of the medium to be tested can be further derived. Finally, the result is displayed on the display 112.

Similarly, the present invention can be applied to the angle measurement, if the refractive index ratio n is known, we rewritten the Eq. (7) as $$\theta_i = \sin^{-1}\left[n_1 \sin\left(\sin^{-1}\sqrt{x} - \theta_p\right)\right] \quad (9)$$

wherein $$x = \frac{(1+n^2) - \sqrt{(1+n^2)^2 - 4n^2(1 + \tan^2(\phi/2))}}{2(1 + \tan^2(\phi/2))} \quad (10)$$

Therefore, the angle $\theta_i$ can be obtained via substituting the measured by the phase meter 110 into Eq. (9) and (10) and calculating by the personal computer or the automatic operation processing hardware.

As to the measurements of other physical values such as pressure and temperature, as long as the physical values will cause the change of the refractive index and incident angle, the present invention can be applied. When the medium to be tested is effected by some physical values and then the refractive index or the incident angle is changed, the physical value of the medium to be tested can be obtained by finding out the relation between the physical variation and the refractive index/incident angle and calculating it via the above-mentioned equations.

The present invention firstly discloses a new measuring method which can apply to a plurality of fields. Besides, the present invention is a common path structure. The present invention not only has the advantage of heterodyne interferometry but also overcomes the disadvantages of non-common path structure. Therefore, the obtained result is precise and reliable. Besides, the present invention has high stability against light intensity variation and other scattering light source. Furthermore, the method has several merits such as simple optical setup, easy operation, high measurement accuracy and rapid measurement.

Although the present invention and its advantage have been described in detail, it should be understood that various changes, substitutions and alternations can be made herein without departing from the spirit and scope of the invention as defined by the appended claims.

What is claimed is:

1. An method for measuring physical values, said method being used to measure the phase variation between s-polarization and p-polarization that is due to total internal reflection so as to derive the physical value to be tested, said method comprising the steps of:

selecting a material with a higher refractive index to be a base for total internal reflection and a material with a lower refractive index to be tightly positioned on one side of said base;

adjusting and calibrating the angle of the incident beam;

adjusting the polarization direction of a heterodyne light source so as to meet the s-polarization and p-polarization on the incident surface being both a single frequency and a frequency difference between said polarizations;

receiving the light interference signals on the two light paths;

measuring the phase meter and measuring initial phase difference between said two light paths;

selecting a suitable angle so that the boundary to be tested meeting the total internal reflection condition; and calculating the phase difference by a phase meter and calculating said physical values of said medium to be tested according to said phase difference.

2. The method according to claim 1, wherein said light paths each comprises an analyzer with a transmission axis at 45°.

3. The method according to claim 1, wherein said physical value is the refractive index of said medium to be tested.

4. The method according to claim 1, wherein said physical value is the angle of said medium to be tested.

5. The method according to claim 1, wherein said physical value is the temperature of said medium to be tested.

6. The method according to claim 1, wherein said physical value is the pressure of said medium to be tested.

7. The method according to claim 1, wherein said two light paths for receiving interference signals each comprises an analyzer and a photodetector.

\* \* \* \* \*